United States Patent [19]
Jenker et al.

[11] Patent Number: 5,869,728
[45] Date of Patent: Feb. 9, 1999

[54] PROCESS FOR PREPARING FLUOROALKYL-CONTAINING ORGANOSILICON COMPOUNDS, AND THEIR USE

[75] Inventors: Peter Jenker; Albert-Johannes Frings; Michael Horn; Jaroslaw Monkiewicz, all of Rheinfelden; Burkhard Standke, Loerrach, all of Germany

[73] Assignee: Huels Aktiengesellschaft, Marl, Germany

[21] Appl. No.: 955,290

[22] Filed: Oct. 21, 1997

[30] Foreign Application Priority Data

Oct. 26, 1996 [DE] Germany .................. 196 44 561.2

[51] Int. Cl.$^6$ .......................................... C07F 7/08
[52] U.S. Cl. .................. 556/479; 556/465; 556/485; 556/454; 556/450; 556/457; 556/458; 528/15
[58] Field of Search .................. 556/465, 485, 556/479, 454, 450, 457, 458; 528/15

[56] References Cited

U.S. PATENT DOCUMENTS

| | | | |
|---|---|---|---|
| 5,142,037 | 8/1992 | Yamazaki et al. | 556/479 |
| 5,463,009 | 10/1995 | Okada et al. | 556/479 |
| 5,561,231 | 10/1996 | Dauth et al. | 556/479 |
| 5,639,845 | 6/1997 | Inomata et al. | 556/479 |
| 5,654,455 | 8/1997 | Pastor et al. | 556/479 X |
| 5,663,399 | 9/1997 | Furukawa et al. | 556/479 |
| 5,756,795 | 5/1998 | Bank et al. | 556/479 |

FOREIGN PATENT DOCUMENTS

| | | |
|---|---|---|
| 0 075 864 | 4/1983 | European Pat. Off. . |
| 0 075 865 | 4/1983 | European Pat. Off. . |
| 0 416 471 | 3/1991 | European Pat. Off. . |
| 0 466 958 A1 | 1/1992 | European Pat. Off. . |
| 0 538 061 A2 | 4/1993 | European Pat. Off. . |
| 0 573 282 A1 | 12/1993 | European Pat. Off. . |
| 0 596 646 | 8/1994 | European Pat. Off. . |
| 0 611 771 | 8/1994 | European Pat. Off. . |
| 0 652 222 | 5/1995 | European Pat. Off. . |
| 0 688 777 | 12/1995 | European Pat. Off. . |
| 0 690 067 | 1/1996 | European Pat. Off. . |
| 1 941 411 A | 12/1970 | Germany . |
| 31 03 705 A1 | 11/1981 | Germany . |
| WO 94/20442 | 9/1994 | WIPO . |

OTHER PUBLICATIONS

Chemical Abstract 90–256447/34.
Chemical Abstract 94–313698/39.
Chemical Abstract 91–175148/24.
Patent Abstracts of Japan, vol. 18, Nr. 625 (88 C 1279), 1994, JP 6–239872 A (Shin Etsu Chem).
Patent Abstracts of Japan, vol. 14, Nr. 453 (49 C 764), 1990, JP 2–178292 A (Takeo Konakahara).

*Primary Examiner*—Paul F. Shaver
*Attorney, Agent, or Firm*—Oblon, Spivak, McClelland, Maier & Neustadt, P.C.

[57] ABSTRACT

Fluoroalkyl organosilicon compounds are prepared by reacting fluoroolefins with organosilicon compounds that contain at least one H—Si group, in the presence of a Pt(0) complex catalyst. Further, fluoroalkylalkoxy organosilicon compounds are prepared by esterifying fluoroalkyl organosilicon compounds. The process proceeds uniformly under mild conditions with high yields and selectivities.

20 Claims, No Drawings

PROCESS FOR PREPARING FLUOROALKYL-CONTAINING ORGANOSILICON COMPOUNDS, AND THEIR USE

BACKGROUND OF THE INVENTION

1. Field of the Invention

The invention relates to processes for preparing fluoroalkyl organosilicon compounds by reacting fluorine-containing olefins with organosilicon compounds in the presence of a platinum catalyst.

2. Discussion of the Background

In recent years, a large number of new applications have been discovered for fluoroalkylchlorosilanes and fluoroalkylalkoxysilanes. These compounds are useful as surfactants to modify the surfaces of lenses and optical fibers or for producing oil-, dirt-, and water-repellent surfaces, as lubricants, as primers for fluoro resins, as ingredients in cosmetic preparations, and as modifiers in fluoro-rubbers and silicone rubbers.

Platinum catalysts are often used for hydrosilylation reactions of fluoroolefins to produce the above-mentioned silanes. Typically, the preferred catalysts are those in which platinum is in the (+4) oxidation state. However, these Pt(IV) catalyst systems suffer from a number of disadvantages.

In many cases, the reactions are required to run under a closed system. JP 02 178 292 A2 discloses the reaction of $F_3C(CF_2)_2C(CF_3)_2CH_2CHCH_2$ with $HSiCl_3$ in a blown glass tube in the presence of a $H_2PtCl_6$ catalyst at a temperature of 100° C. for 3 h with a yield of 83% EP 0 538 061 A2 discloses a reaction of $CF_3CF_2CF_2OCF(CF_3)$ $CF_2OCF_2CF_2CHCH_2$ with $CH_3SiHCl_2$ in the presence of $H_2PtCl_6$ in a steel autoclave at a reaction temperature of 120° C., with a reaction period of 20 h and a resulting yield of 67%.

At atmospheric pressure, such reactions are relatively lengthy. For instance, JP 06 239 872 A2 discloses a reaction time of 48 h for the reaction of $C_3F_7O[CF(CF_3)CF_2O]_3CF$ $(CF_3)CHCH_2$ with $(CH_3)_{3-n}SiHCl_n$ (n=1,2) in the presence of $H_2PtCl_6$ at a reaction temperature of 150° C., resulting in a yield of 88%. WO 94/20442 discloses a yield of 89% and a reaction period of 50 h for a hydrosilylation reaction, at a reaction temperature of 100° C. in the presence of $H_2PtCl_6$.

The reactions may not be stereospecific. WO 94/20442 additionally discloses that, for example, in the hydrosilylation reaction of $p-CF_3C_6H_4CHCH_2$ with $CH_3SiHCl_2$, isomerization may occur with a concomitant reduction in selectivity. In this case, an 87:13 ratio of β-silylated to α-silylated fluoroolefin is obtained with a yield of 89%.

To raise the selectivity and reactivity, and in some cases to improve the solubility of the platinum compound, complexing reagents are added to the platinum catalyst. For example, JP 03 106 889 A2 teaches the addition of acetone. EP 0 466 958 A1 discloses isopropanol as an additive, while EP 0 573 282 A1 discloses the use of $H_2PtCl_6$ in 2-ethylhexanal. It is also known to add m-xylene hexafluoride to the Pt catalyst (EP 0 573 282 A1). However, in all of these examples, the cost and complexity of preparation are considerable.

In general, none of the above-mentioned catalyst systems are sufficiently reactive or selective, with the result that, from an economic standpoint, such processes are of little interest for the preparation of fluoroalkyl-containing organosilicon compounds.

SUMMARY OF THE INVENTION

One object of the present invention is to provide a process for preparing fluoroalkyl organosilicon compounds simply and economically.

Another object of the present invention is to provide a process for preparing fluoroalkyl organosilicon compounds under mild reaction conditions with high yields and high selectivity.

Another object of the present invention is to provide a process for preparing fluoroalkyl organosilicon compounds using KARSTEDT catalysts.

Another object of the present invention is to provide a process which proceeds uniformly under atmospheric pressure and at low temperatures.

Another object of the present invention is to provide a process which does not require an excess amount of organosilicon reactant, thereby minimizing the proportion of byproducts that require separation and disposal.

Another object of the present invention is to provide a process for preparing fluoroalkyl organosilicon compounds in which unwanted isomerization is reduced or eliminated.

Another object of the present invention is to provide a process for preparing fluoroalkylalkoxy organosilicon compounds.

Another object of the present invention provides for surface-treating agents for enhancing the surface of plastics, glass, metals, ceramics and stone; textile auxiliaries; and architectural preservative preparations which contain fluoroalkyl organosilicon compounds produced by the process.

These and other objects of the present invention have been achieved by reacting, in the presence of a Pt(0) complex catalyst, at least one fluoroolefin with at least one organosilicon compound that contains at least one H—Si group.

The first embodiment of the invention relates to a process for preparing fluoroalkyl organosilicon compounds, which includes:

reacting, in the presence of a Pt(0) complex catalyst,
at least one fluoroolefin with
at least one organosilicon compound that contains at least one H—Si group.

The second embodiment of the invention relates to a process for preparing a fluoroalkylalkoxy organosilicon compound, which includes:

reacting, in the presence of a Pt(0) complex catalyst,
at least one fluoroolefin with
at least one organosilicon compound that contains at least one H—Si group; and
esterifying with an alcohol.

The third embodiment of the invention relates to a fluoroalkyl organosilicon compound prepared by a process which includes:

reacting, in the presence of a Pt(0) complex catalyst,
at least one fluoroolefin with
at least one organosilicon compound that contains at least one H—Si group.

By means of the present invention, fluoroalkyl and fluoroalkylalkyoxy organosilicon compounds can be produced with yields of up to 99%. Heretofore, it was completely unexpected that a process of reacting at least one fluoroolefin with at least one organosilicon compound that contains at least one H—Si group, in the presence of a Pt(0) complex catalyst, would proceed so uniformly, under such mild conditions, and with such improved reactivity, selectivity, and yield.

DESCRIPTION OF THE PREFERRED EMBODIMENTS

Other features of the invention will become apparent in the course of the following descriptions of exemplary embodiments which are given for illustration of the invention and are not intended to be limiting thereof In the present process, it is preferred to employ a Pt(0) complex catalyst of the KARSTEDT type. More preferably, the KARSTEDT catalyst is selected from the group consisting of bis[1,3-bis(eta-2-ethenyl)-1,1,3,3-tetramethyldisiloxane]platinum(0), triphenylphosphine-[1,3-bis(eta-2-ethenyl)-1,1,3,3-tetramethyldisiloxane]platinum(0) and 2,4,6,8-tetraethenyl-2,4,6,8-tetramethylcyclotetrasiloxane platinum(0). Preferred KARSTEDT catalysts are those which contain 0.01–20% by weight of platinum, based on the weight of the catalyst, preferably 0.1–10% by weight of platinum and, more preferably 0.5–5% by weight of platinum These ranges include all specific values and subranges therebetween. The catalyst system can be dissolved in an inert solvent. Suitable solvents are xylene (o-, m-, and p-) and toluene. Other inert solvents may be used that are known in the art having boiling points between 100°–200° C., preferably 110°–160° C., and more preferably 110°–145° C. These ranges include all specific values and subranges therebetween.

DE-A 1 941 411, FR-A 2 474 890 and U.S. Pat. No. 3,775,452 disclose platinum catalysts of the KARSTEDT type, the contents of each are hereby incorporated by reference.

The present reaction is preferably carried out employing at least one fluoroolefin of the general formula (I)

$$R^1YCH=CH_2 \tag{I}$$

in which $R^1$ is a mono-, oligo-, or perfluorinated alkyl group having 1 to 20, preferably 1 to 9 carbon atoms or a mono-, oligo-, or perfluorinated aryl group having 6 to 10, preferably 6 carbon atoms and Y is a —$CH_2$—, —O— or —S— group. Examples are —$CF_3(CF_2)_n CHCH_2$ where n=3,5,7 and 9, $HCF_2CF_2OCH_2CHCH_2$, and $R_fCH_2CH_2O(CO)(C(CH_3))CH_2$ where $R_f=C_nF_{2n+1}$, in which n=2 to 18.

The organosilicon compound that contains at least one H—Si group is preferably a hydrosilane of the general formula (II):

in which $R_2$ is identical or different alkyl groups of 1 to 20 carbon atoms, preferably methyl or ethyl, or aryl groups having 6 to 10 carbon atoms, preferably phenyl, X is a Cl or Br, and a=0, 1, 2, or 3 and b=0, 1, 2 or 3 where $1 \leq (a+b) \leq 3$;

or a disiloxane of the general formula (III):

in which $R^2$ is identical or different alkyl groups of 1 to 20 carbon atoms, preferably methyl or ethyl, or aryl groups having 6 to 10 carbon atoms, preferably phenyl, X is independently in each case a Cl or Br, and a=0, 1 or 2, and b=0, 1, or 2 where $1 \leq (a+b) \leq 2$;

or a cyclic siloxane of the general formula (IV):

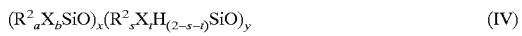

in which $R^2$ is identical or different alkyl groups of 1 to 20 carbon atoms, preferably methyl or ethyl, or aryl groups having 6 to 10 carbon atoms, preferably phenyl, X is independently in each case a Cl or Br, a=0, 1, or 2 and b=0, 1, or 2 where (a+b)=2, and x adopts a value from 0 to 5, s=0 or 1 and t=0 or 1 where $0 \leq (s+t) \leq 1$, and y adopts a value from 1 to 5 where $3 \leq (x+y) \leq 5$;

or linear polysiloxane mixtures of the general formula (V)

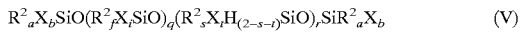

where $R^2$ identical or different alkyl groups of 1 to 20 carbon atoms, preferably methyl or ethyl, or aryl groups having 6 to 10 carbon atoms, preferably phenyl, X is independently in each case a Cl or Br, a=0, 1, 2, or 3 and b=0, 1, 2, or 3 where (a+b)=3, f=0, 1 or 2 and i=0, 1 or 2 where (f+i)=2, and $q \geq 0$, s=0 or 1 and t=0 or 1 where $0 \leq (s+t) \leq 1$ and $r \geq 1$ where $50 \leq (q+r) \leq 50,000$, preferably 5,000 to 10,000.

The organosilicon compound that contains at least one H—Si group is more preferably $HSiCl_3$, $HSiCH_3Cl_2$ or $HSi(CH_3)_2Cl$.

In the starting mixture, the total amount of platinum relative to the total amount of the fluoroolefin is preferably in a weight ratio of 1:100 to 1:100,000, preferably in a ratio of 1:1,000 to 1:30,000 and most preferably in a ratio of 1:5,000 to 1:20,000. More preferably, in the starting mixture, the total amount of the platinum relative to the total amount of the fluoroolefin having the general formula (I) is preferably in a weight ratio of 1:100 to 1:100,000, preferably in a ratio of 1:1,000 to 1:30,000 and most preferably in a ratio of 1:5,000 to 1:20,000. These ranges include all specific values and subranges therebetween.

The fluoroolefin is preferably first charged into a vessel, which can be both heated and cooled, has a stirring device and reflux condenser, and equipped to run under nitrogen, argon, or another inert atmosphere. The Pt(0) catalyst, preferably dissolved in a solvent, is then added.

The organosilicon compound that contains at least one H—Si group can then be supplied to the reaction vessel by way of a metering device.

The addition of the organosilicon compound that contains at least one H—Si group to the fluoroolefin is generally commenced at room temperature. The heat produced during this addition may be completely sufficient to drive the reaction. Alternatively, heat may be applied to the reaction from an outside source. Since a heat source is not necessarily required, however, and the reaction proceeds even under atmospheric pressure, the expenditure on apparatus is generally low. Because the reactivity and selectivity of the process is high, an excess of the organosilicon compound that contains at least one H—Si group is generally not required, thus also minimizing the proportion of byproducts and reactants which may remain, and require disposal, after the process has been carried out.

When conducting the present process on a laboratory scale (500 ml), the addition of the organosilicon compound that contains at least one H—Si group generally takes place over a period of 20 to 120 minutes, preferably from 30 to 60 minutes. These ranges include all specific values and subranges therebetween. The reaction mixture may be stirred during the addition of the organosilicon compound that has at least one H—Si group, which stirring may be continued after completion of the addition. In general, stirring is continued for 1 to 5 h, preferably 1 to 3 h, more preferably 1 to 1.5 h. These ranges include all specific values and subranges therebetween. The addition time and stirring time may be scaled up as necessary to effect the process on a larger scale.

The reaction is preferably carried out at a temperature in the range of 10° to 200° C., more preferably 20° to 150° C. The pressure is in the range of 1 to 50 bar abs., preferably 1 to 10 bar abs. These ranges include all specific values and subranges therebetween.

After the reaction is complete, the fluoroalkyl organosilicon compound is recovered from the reaction mixture. Preferably, the reaction mixture can be worked up by distillation.

It is thus possible, simply and economically and in accordance with the process, to prepare, for example, 3,3,4,4,5,5,6,6,7,7,8,8,9,9,10,10,10-heptadecafluorooctyltrichlorosilane, 3,3,4,4,5,5,6,6,7,7,8,8,8-tridecafluorooctylmethyldichlorosilane and 3-(1,1,2,2-tetrafluoroethoxy)propyltrichlorosilane.

The process offers the advantage of synthesizing fluoroalkyl organosilicon compounds under mild reaction conditions, with high yields and high selectivity, and using low concentrations of catalyst. In the process, there are generally no instances either of isomerization of the double bond in the course of the addition reaction with, for example, trichlorosilanes, alkylchlorosilanes or arylchlorosilanes, or of isomerization of the fluoroalkyl radicals. Further advantages of the present process are the short reaction times and the uniform progression of the reaction.

Fluoroalkyl organosilicon compounds that contain at least one Cl—Si group or Br—Si group that may be obtained by the present process can be esterified with an alcohol to give the corresponding alkoxy-Si compounds. Preferred alcohols include methanol, ethanol, n-propanol, i-propanol, n-butanol, i-butanol, t-butanol or 2-methoxyethanol. In this case, the reaction mixture that contains the fluoroalkyl organosilicon compound can be used without further purification as the starting material for the esterification of the Cl—Si or Br—Si groups with an alcohol. The esterification step proceeds uniformly. The separation of any remaining highly volatile fractions may be effected by simple distillation, giving fluoroalkylalkoxy organosilicon compounds with a purity of from 98.5 to 99.9% by area GC-TCD (=percent of the integrated peak area in the chromatogram with detection by thermal conductivity detector), for example, 3,3,4,4,5,5,6,6,7,7,8,8,8-tridecafluorooctyltrichlorosilane.

The present invention, therefore, also provides a process for preparing fluoroalkylalkoxy organosilicon compounds of the general formula (VI):

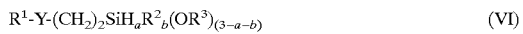

in which
R$^1$ is a mono-, oligo-, or perfluorinated alkyl group of 1 to 20, preferably 1 to 9 carbon atoms or a mono-, oligo-, or perfluorinated aryl group having 6 to 10 carbon atoms, preferably $CF_3(CF_2)_7$—, $CF_3(C_6H_4)$—, $C_6F_5$—, $R_fCH_2CH_2(CO)$—($R_f=C_nF_{2n+1}$ where n=2 to 18), and Y is a $CH_2$, O or S group.

R$^2$ is an alkyl group of 1 to 20, preferably 1 to 8 carbon atoms or an aryl group having 6 to 10 carbon atoms, R$^3$ is an alkyl group of 1 to 20, preferably 1 to 8 carbon atoms or an aryl group having 6 to 10 carbon atoms, and a=0, 1 or 2 and b=0, 1 or 2 where(a+b)≦2, which includes reacting a fluoroalkyl organosilicon compound that contains at least one Cl—Si or Br—Si group with a monohydric alcohol and recovering the fluoroalkylalkoxy organosilicon compound of the general formula (VI) from the reaction mixture.

EXAMPLES

Having generally described this invention, a further understanding can be obtained by reference to certain specific examples which are provided herein for purposes of illustration only and are not intended to be limiting unless otherwise specified.

Example 1

126 g (0.8 mol) of 1,1,2,2-tetrafluoroethyl allyl ether are charged under an N$_2$ atmosphere to a 500 ml three-necked glass flask provided with top-mounted water condenser, magnetic stirrer, thermometer and dropping funnel, and 0.4 g of CPC 072 (Pt(0)-divinyltetramethyldisiloxane in xylene; concentration Pt: 1,1,2,2-tetrafluoroethyl allyl ether 1:20,000) are added. 108 g (0.8 mol) of trichlorosilane are added dropwise at room temperature and with stirring over a period of 80 minutes. The immediately ensuing reaction is exothermic, the temperature rising to 110° C. After the end of the addition, the reaction mixture is stirred for 1 h more and then analyzed by GC. After subsequent distillative purification over a short-path column, 225 g (0.77 mol) of 3-(1,1,2,2-tetrafluoroethoxy)propyltrichlorosilane are obtained (yield-. 96%, purity: >98 area % GC-TCD).

Example 2

192 g (0.55 mol) of 3,3,4,4,5,5,6,6,7,7,8,8,8-tridecafluorooctene are charged under an N$_2$ atmosphere to a 500 ml three-necked glass flask provided with top mounted water condenser, magnetic stirrer, thermometer and dropping funnel, and 0.3 g of CPC 072 (Pt(0)-divinyltetramethyidisiloxane in xylene, concentration Pt: 3,3,4,4,5,5,6,6,7,7,8,8,8-tridecafluorooctene=1:20,000) are added. 80 g (0.59 mol) of trichlorosilane are added dropwise at room temperature and with stirring over a period of 85 minutes. The immediately ensuing reaction is exothermic, the temperature rising to 115° C. After the end of the addition, the reaction mixture is stirred for 1.5 h more and then analyzed by GC. After subsequent distillative purification over a short-path column, 262 g (0.54 mol) of 3,3,4,4,5,5,6,6,7,7,8,8,8-tridecafluorooctyltrichlorosilane are obtained (yield: 99%, purity: >97 area % GC-TCD).

Example 3

123 g (0.5 mol) of 3,3,4,4,5,5,6,6,6-nonafluorohexene and 76 g (0.5 mol) of trichlorosilane together with 0.34 g of CPC 072 (Pt(0)-divinyltetramethyldisiloxane in xylene; concentration Pt:3,3,4,4,5,5,6,6,6-nonafluorohexene=1:20,000) are charged to a 250 ml laboratory steel autoclave. The autoclave is closed and heated to 140° C. in an oil bath over 70 minutes. The exothermic reaction begins after about 8 minutes, the reaction mixture rising to 165° C. It is subsequently cooled, the reactor is emptied, and short-path distillation gives 176 g (0.46 mol) of 3,3,4,4,5,5,6,6,6-nonafluorohexyltrichlorosilane (yield: 90%, purity: >98 area % GC-TCD).

Example 4

544 g (1.83 mol) of 3-(1,1,2,2-tetrafluoroethoxy) propyltrichlorosilane are charged to a 1,000 ml three-necked glass flask provided with top-mounted water condenser, magnetic stirrer, thermometer and dropping funnel, and 256 g (5.57 mol) of ethanol are added dropwise over 6.5 h with stirring. The reaction proceeds exothermically, the reaction mixture rising to 110° C. 165 g of NaOEt solution (21% in ethanol) are then added over a further 90 minutes. After cooling, the NaCl formed is filtered off and the filtrate is distilled over a short-path column. 519 g (1.61 mol) of 3-(1,1,2,2-tetrafluoroethoxy)propyltriethoxysilane are obtained (yield: 90%, purity: >98 area % GCTCD).

The entire contents of German patent application 196 44 561.2, filed Oct. 26, 1996, are hereby incorporated by reference.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A process for preparing fluoroalkyl organosilicon compounds comprising:
   reacting, in the presence of a Pt(0) complex catalyst,
   at least one fluoroolefin with
   at least one organosilicon compound that contains at least one H—Si group.

2. The process as claimed in claim 1, wherein said Pt(0) complex catalyst comprises a KARSTEDT catalyst.

3. The process as claimed in claim 1, wherein said Pt(0) complex catalyst contains 0.01 to 20% by weight of platinum.

4. The process as claimed in claim 2, wherein said KARSTEDT catalyst is selected from the group consisting of bis[1,3-bis(eta-2-ethenyl)-1,1,3,3-tetramethyidisiloxane] platinum(0), triphenylphosphine-[1,3bis(eta-2-ethenyl)-1,1,3,3-tetramethyldisiloxane]platinum(0) and 2,4,6,8-tetraethenyl-2,4,6,8-tetramethylcyclotetrasiloxaneplatinum (0).

5. The process as claimed in claim 1, wherein said fluoroolefin comprises a fluorolefin having the general formula (I):

$$R^1YCH{=}CH_2 \qquad (I)$$

wherein $R^1$ is a mono-, oligo-, or perfluorinated alkyl group having 1 to 20 carbon atoms or a mono-, oligo-, or perfluorinated aryl group having 6 to 10 carbon atoms, and Y is a —CH$_2$—, —O— or —S— group.

6. The process as claimed in claim 1, wherein said organosilicon compound that contains at least one H—Si group comprises a hydrosilane having the general formula (II):

$$H_{(4-a-b)}SiR^2{}_aX_b \qquad (II)$$

wherein
$R^2$ is identical or different alkyl groups having 1 to 20 carbon atoms or aryl groups having 6 to 10 carbon atoms, X is independently Cl or Br, and a=0, 1, 2, or 3 and b=0, 1, 2, or 3 wherein $1{\leq}(a+b){\leq}3$.

7. The process as claimed in claim 1, wherein said organosilicon compound that contains at least one H—Si group comprises a disiloxane having the general formula (III):

$$R^2{}_aX_bH_{(3-a-b)}SiOSiH_{(3-a-b)}R^2{}_aX_b \qquad (III)$$

wherein
$R^2$ is identical or different alkyl groups of 1 to 20 carbon atoms or aryl groups having 6 to 10 carbon atoms, X is independently Cl or Br, and a=0, 1, or 2 and b=0, 1, or 2 wherein $1{\leq}(a+b){\leq}2$.

8. The process as claimed in claim 1, wherein organosilicon compound that contains at least one H—Si group comprises a cyclic siloxane having the general formula (IV):

$$(R^2{}_aX_bSiO)_x(R^2{}_sX_tH_{(2-s-t)}SiO)_y \qquad (IV)$$

wherein
$R^2$ is identical or different alkyl groups of 1 to 20 carbon atoms or aryl groups having 6 to 10 carbon atoms, X is independently Cl or Br, a=0, 1, or 2 and b=0, 1, or 2 where (a+b)=2, and x is 0 to 5, s=0 or 1 and t=0 or 1 where $0{\leq}(s+t){\leq}1$, and y is 1 to 5 wherein $3{\leq}(x+y){\leq}5$.

9. The process as claimed in claim 1, wherein said organosilicon compound that has at least one H—Si group comprises a linear polysiloxane having the general formula (V):

$$R^2{}_aX_bSiO(R^2{}_fX_iSiO)_q(R^2{}_sX_tH_{(2-s-t)}SiO)_rSiR^2{}_aX_b \qquad (V)$$

wherein
$R^2$ is identical or different alkyl groups of 1 to 20 carbon atoms or aryl groups having 6 to 10 carbon atoms, X is Cl or Br, a=0, 1, 2, or 3 and b=0, 1, 2, or 3 wherein (a+b)=3, f=0, 1, or 2 and i=0, 1, or 2 wherein (f+i)=2, and q${\geq}$0, s=0 or 1 and t=0 or 1 wherein $0{\leq}(s+t){\leq}1$ and r${\geq}$1 wherein $50{\leq}(q+r){\leq}50{,}000$.

10. The process as claimed in claim 1, wherein the weight ratio of the total amount of platinum to the total amount of said fluoroolefin is 1:100 to 1:100,000.

11. The process as claimed in claim 1, wherein the reaction is carried out at a temperature of 10° to 200° C.

12. The process as claimed in claim 1, wherein the reaction is carried out at a pressure of 1 to 50 bar abs.

13. The process as claimed in claim 1, further comprising esterifying the obtained fluoroalkyl organosilicon compounds with an alcohol selected from the group consisting of methanol, ethanol, n-propinol, i-propanol, n-butanol, i-butanol, t-butanol, 2-methoxyethanol, and mixtures thereof.

14. The process as claimed in claim 1, further comprising purifying the obtained fluoroalkyl organosilicon compounds by distillation.

15. A process for preparing a fluoroalkylalkoxy organosilicon compound having the general formula (VI):

$$R^1\text{-}Y\text{-}(CH_2)_2SiH_aR^2{}_b(OR^3)_{(3-a-b)} \qquad (VI)$$

wherein
$R^1$ is a mono-, oligo-, or perfluorinated alkyl group having 1 to 20 carbon atoms or a mono-, oligo-, or perfluorinated aryl group having 6 to 10 carbon atoms, and Y is a —CH$_2$—, —O—, or —S— group, $R^2$ is identical or different alkyl groups having 1 to 20 carbon atoms or aryl groups having 6 to 10 carbon atoms, $R^3$ is an alkyl group having 1 to 20 carbon atoms or an aryl group having 6 to 10 carbon atoms, and a=0, 1, or 2 and b=0, 1, or 2 wherein $(a+b){\leq}2$, comprising the steps of:
reacting, in the presence of a Pt(0) complex catalyst, at least one fluoroolefin with at least one organosilicon compound that contains at least one H—Si group;
esterifying with an alcohol; and
purifying by distillation a fluoroalkylalkoxy organosilicon compound having the general formula (VI):

$$R^1\text{-}Y\text{-}(CH_2)_2SiH_aR^2_b(OR^3)_{(3-a-b)} \quad (VI)$$

wherein $R^1$ is a mono-, oligo-, or perfluorinated alkyl group having 1 to 20 carbon atoms or a mono-, oligo-, or perfluoriniated aryl group having 6 to 10 carbon atoms, and Y is a —CH$_2$—, —O—, or —S— group, $R^2$ is identical or different alkyl groups having 1 to 20 carbon atoms or aryl groups having 6 to 10 carbon atoms, $R^3$ is an alkyl group having 1 to 20 carbon atoms or an aryl group having 6 to 10 carbon atoms, and a=0, 1, or 2 and b=0, 1, or 2 wherein (a+b)≦2.

16. The process as claimed in claim 15, wherein said Pt(0) complex catalyst comprises a KARSTEDT catalyst.

17. The process is claimed in claim 15, wherein said fluoroolefin comprises a fluoroolefin having the general formula (1):

$$R^1YCH=CH_2 \quad (I)$$

wherein $R^1$ is a mono-, oligo-, or perfluorinated alkyl group having 1 to 20 carbon atoms or a mono-, oligo-, or perfluorinated aryl group having 6 to 10 carbon atoms, and Y is a —CH$_2$—, —O— or —S— group.

18. The process as claimed in claim 15, wherein said organosilicon compound that contains at least one H—Si group comprises a hydrosilane having the general formula (II):

$$H_{(4-a-b)}SiR^2_aX_b \quad (II)$$

wherein $R^2$ is identical or different alkyl groups having 1 to 20 carbon atoms or aryl groups having 6 to 10 carbon atoms, X is independently Cl or Br, and a=0, 1, 2, or 3 and b=0, 1, 2, or 3 wherein 1≦(a+b)≦3.

19. A fluoroalkyl organosilicon compound produced by a process comprising:
reacting, in the presence of a Pt(0) complex catalyst, at least one fluoroolefin with at least one organosilicon compound that contains at least one H—Si group.

20. A surface-treating agent, comprising the fluoroalkyl organosilicon compound prepared by the process of claim 18.

* * * * *

UNITED STATES PATENT AND TRADEMARK OFFICE
CERTIFICATE OF CORRECTION

PATENT NO.    : 5,869,728
DATED         : February 9, 1999
INVENTOR(S)   : Peter JENKNER, et al.

It is certified that error appears in the above-indentified patent and that said Letters Patent is hereby corrected as shown below:

On the title page, item [75], the 1st inventor's name is incorrect. It should be:

--Peter Jenkner--

Signed and Sealed this

Twenty-third Day of November, 1999

Attest:

Q. TODD DICKINSON

*Attesting Officer*        *Acting Commissioner of Patents and Trademarks*